United States Patent
Matsuo et al.

(10) Patent No.: US 7,962,292 B2
(45) Date of Patent: Jun. 14, 2011

(54) SAMPLE ANALYZER AND SAMPLE ANALYZING METHOD

(75) Inventors: Naohiko Matsuo, Kobe (JP); Hiroyuki Fujino, Kakogawa (JP); Mitsuyo Koya, Kyoto (JP); Susumu Hoshiko, Kobe (JP)

(73) Assignee: Sysmex Corporation, Kobe (JP)

( * ) Notice: Subject to any disclaimer, the term of this patent is extended or adjusted under 35 U.S.C. 154(b) by 680 days.

(21) Appl. No.: 12/012,431

(22) Filed: Jan. 31, 2008

(65) Prior Publication Data

US 2008/0183431 A1    Jul. 31, 2008

(30) Foreign Application Priority Data

Jan. 31, 2007 (JP) ................. 2007-020942

(51) Int. Cl.
*G01N 31/00* (2006.01)
(52) U.S. Cl. ............... 702/22; 702/32; 356/39; 436/69
(58) Field of Classification Search ............. 702/21, 702/22, 27, 28, 30–32, 176; 436/2, 34, 69; 600/368, 369; 356/39, 40, 42
See application file for complete search history.

(56) References Cited

U.S. PATENT DOCUMENTS

| 3,963,909 A | 6/1976 | Atwood et al. |
| 4,217,107 A * | 8/1980 | Saito et al. ............ 436/69 |
| 7,276,376 B2 | 10/2007 | Katayama et al. |

FOREIGN PATENT DOCUMENTS

| JP | 06-249855 | 9/1994 |
| JP | 10-123140 | 5/1998 |

OTHER PUBLICATIONS

Office Action from counterpart Chinese Application No. 200810004754.9, dated Aug. 7, 2009, 2 pages (translation).

* cited by examiner

*Primary Examiner* — Manuel L Barbee
(74) *Attorney, Agent, or Firm* — Brinks Hofer Gilson & Lione (57) ABSTRACT

A sample analyzer optically measures reaction of a sample mixed with reagent, and obtains optical information therefrom; generates a reaction curve representing change in the optical information over time; determines a first area prior to an evaluation target time (t0) and a second area after the evaluation target time (t0) wherein the first and second areas are formed between a baseline which is parallel to the time axis and a reaction curve from a first time (t1) prior to the optional evaluation target time (t0) to a second time (t2) after the evaluation target time, and determines the reaction end point based on the first and second areas; and obtains a characteristic of a sample based on the determined reaction end point, is disclosed. a sample analyzing method is also disclosed.

20 Claims, 10 Drawing Sheets

| Item | Reagent | Interval | |
|---|---|---|---|
| | | t0-t1 | t2-t0 |
| A | α | x | y |
| B | β | x' | y' |
| ⋮ | ⋮ | ⋮ | ⋮ |

FIG.10

SAMPLE ANALYZER AND SAMPLE ANALYZING METHOD

RELATED APPLICATIONS

This application claims priority under 35 U.S.C. §119 to Japanese Patent Application No. JP2007-020942 filed on Jan. 31, 2007, the entire content of which is hereby incorporated by reference.

FIELD OF THE INVENTION

The present invention relates to a sample analyzer and a sample analyzing method which optically measure the reaction of a sample mixed with reagent to obtain the characteristics of the sample.

BACKGROUND

There are various methods for optically measuring a sample and obtaining the characteristics of the sample from the measurement results. One such method optically measures a sample and obtains the coagulation time based on the measurement results. This method uses, for example, blood plasma as a sample to which predetermined reagent is added, and the change in turbidity which occurs in conjunction with the coagulation of the plasma is measured as the change in the amount of transmission light and the amount of scattered light to obtain the blood coagulation.

Japanese Laid-Open Patent Publication No. 10-123140 discloses a blood coagulation analyzer which uses such an optical method. The blood coagulation analyzer radiates light on a blood sample within a transparent container to which reagent has been added, and calculates the coagulation time based on the coagulation saturation value (coagulation reaction end point) from the change in the amount of scattered light over time.

Specifically, the measured value of the amount of scattered light is input to a measuring unit at predetermined time intervals, the latest input value after the coagulation reaction has started is compared to an input value from prior to the predetermined time interval, and the latest input value is set as a provisional saturation value when the difference between the two values (that is, the predetermined time interval (unit time) per amount of change in the input value) is less than a predetermined value (threshold value). Subsequently, the provisional saturation value is set as the true saturation value when there is no further change in the provisional saturation value, and the time to achieve 50% of this change is determined as the coagulation time when change from the amount of scattered light at the start of the coagulation time to the amount of scattered light at the true saturation value is deemed as 100%.

Japanese Laid-Open Patent Publication No. 6-249855 also discloses a blood coagulation analyzer which uses such an optical method. The blood coagulation analyzer radiates light on a blood sample within a transparent container to which reagent has been added, and calculates the coagulation time based on the ratio of the integration values at short intervals of the A/D-converted scattered light data.

Specifically, A/D conversion data obtained by measuring the amount of scattered light are smoothed and the origin point adjusted then set as basic A/D conversion data; the basic ratio data are then calculated, that is, the ratio of integration values of the integrated basic integration data and basic A/D-conversion data at adjacent short intervals is calculated; basic A/D conversion data values are selected to determine the coagulation time from the time at which the basic ratio data reaches preset fixed basic ratio data; and then the time corresponding to the basic A/D conversion data value 1/N (where N is a constant integer of 1 or higher) is determined from the mixing time and set as the coagulation time.

Since the saturation value is determined based on the difference between two input values in the art disclosed in Japanese Laid-Open Patent Publication No. 10-123140, an accurate saturation value can not be determined because there is a large fluctuation in the difference between the two input values and the noise in each input value. Moreover, in some cases of specific measurement items and blood samples (for example, samples with high concentration of fibrin or heparin) which exhibit constant change in the amount of scattered light even after the actual coagulation reaction has ended, it may be difficult to determine the point at which the difference between the two input values becomes less than the threshold value. Thus the determination of the saturation value itself becomes quite difficult.

Furthermore, the art disclosed in Japanese Laid-Open Patent Publication No. 6-249855 is easily affected by fluctuations in the amount of scattered light in the short intervals since the coagulation time is calculated based on the basic ratio data, which is the ratio of the integration values of the basic integration data and the basic A/D conversion data at adjacent short intervals.

SUMMARY OF THE INVENTION

The scope of the present invention is defined solely by the appended claims, and is not affected to any degree by the statements within this summary.

A first aspect of the present invention is a sample analyzer comprising: a measuring means for optically measuring reaction of a sample mixed with reagent, and obtaining optical information therefrom; a generating means for generating a reaction curve representing change in the optical information over time; a determining means for determining a first area prior to an evaluation target time (t0) and a second area after the evaluation target time (t0) wherein the first and second areas are formed between a baseline which is parallel to the time axis and a reaction curve from a first time (t1) prior to the optional evaluation target time (t0) to a second time (t2) after the evaluation target time, and determining the reaction end point based on the first and second areas; and an acquiring means for obtaining a characteristic of a sample based on the determined reaction end point.

A second aspect of the present invention is a sample analyzing method comprising: a measuring step for optically measuring reaction of a sample mixed with reagent, and obtaining optical information therefrom; a generating step for generating a reaction curve which represents change in the optical information over time; a determining step for determining a first area prior to an evaluation target time t0 and a second area after the evaluation target time (t0) wherein the first and second areas are formed between a baseline which is parallel to the time axis and a reaction curve from a first time (t1) prior to the optional evaluation target time (t0) to a second time (t2) after the evaluation target time, and determining the reaction end point based on the first and second areas; and an acquiring step for obtaining a characteristic of a sample based on the determined reaction end point.

A third aspect of the present invention is a sample analyzer comprising: a means for optically measuring reaction of a sample mixed with reagent, and obtaining optical information therefrom; a generating means for generating a reaction curve representing change in the optical information over time; a determining means for determining a reaction end point based on a first value which represents an amount of a predetermined component generated by a reaction in the sample during a predetermined time period prior to an evaluation target time (t0), and a second value representing an amount of the predetermined component generated by a reaction in the sample during a predetermined time period after the evaluation target time (t0); and an acquiring means for obtaining a characteristic of a sample based on the determined reaction end point.

DETAILED DESCRIPTION OF THE PREFERRED EMBODIMENTS

The preferred embodiments of the present invention will be described hereinafter with reference to the drawings.

General Structure of the Sample Measuring Apparatus 1

The sample measuring apparatus 1 of the present embodiment is a blood analyzer for optically measuring and analyzing the amount and degree of activity of specific substances related to blood coagulation and fibrinolytic function, and this analyzer uses blood plasma as a sample. The analyzer 1 optically measures samples using a coagulation time method, synthetic substrate method, and immunoturbidity method (main measurement). The blood coagulation time in the present embodiment is a measurement method in which the process of plasma coagulation is detected as a change in transmitted light. The items measured include TT (thrombin time), PT (prothrombin time), APTT (Active partial thromboplastin time), Fbg (fibrinogen content), LA (lupus anticoagulant) and the like. Measurement criteria of the synthetic substrate method include ATIII and the like, and those of the immunoturbidity method include D-dimer, FDP and the like.

Figure 1:
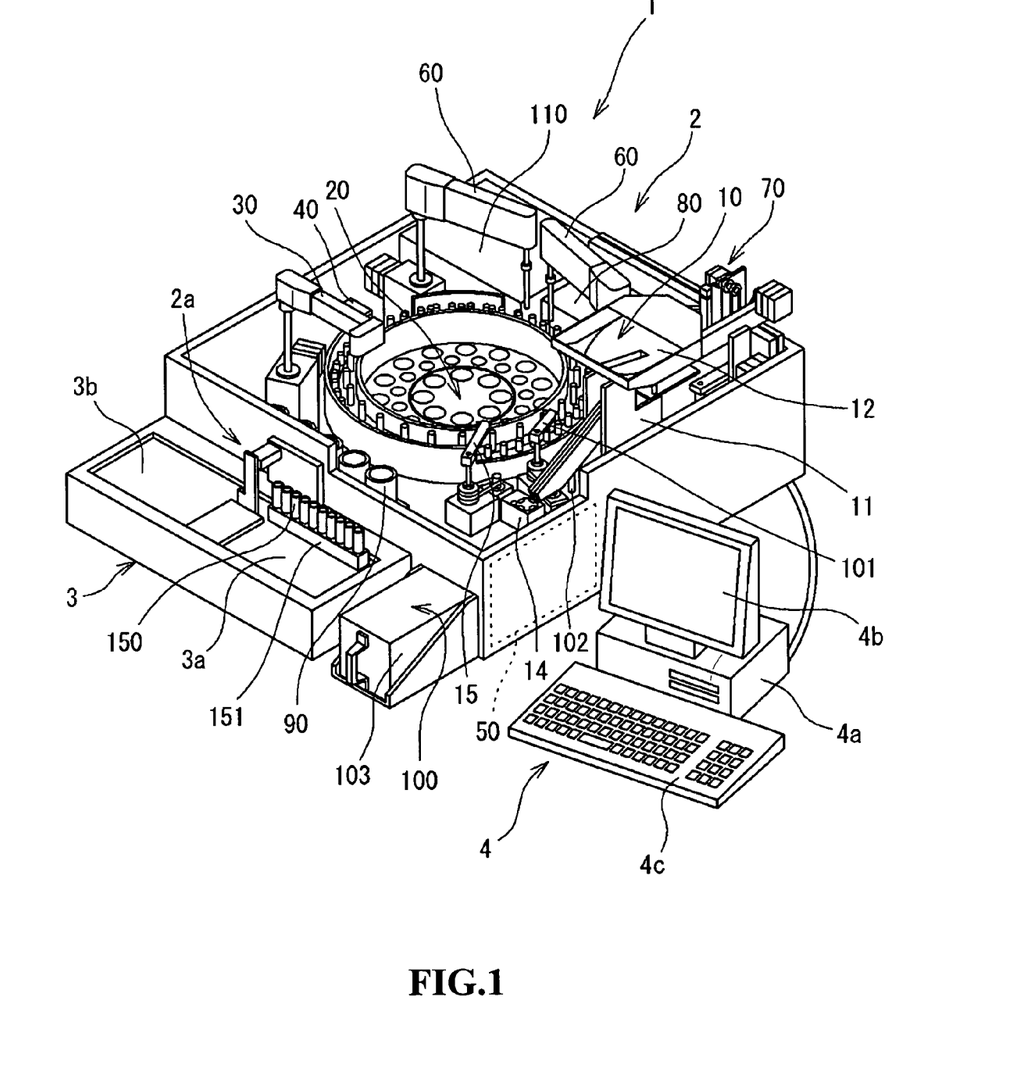
FIG. 1 is a perspective view showing the overall structure of the sample measuring apparatus of an embodiment of the present invention.

As shown in FIG. 1, the analyzer I is mainly configured by a measuring unit which has a measuring unit 2, a transporting unit 3 disposed on the front side of the measuring unit 2, and a control unit 120 for controlling the operations of each mechanism in the measuring unit 2 and transporting unit 3 (refer to FIG. 3), and is further configured by a control device 4, which is a data processing unit, electrically connected to the to the measuring unit 2. Although the transporting unit 3 and measuring unit 2 are integratedly configured as a single unit in the analyzer 1 of the present embodiment, the transporting unit 3 may also be separate from the analyzer 1. In a large-scale system which includes a plurality of analyzers, for example, a modality may be used in which the plurality of analyzers may be connected to a large conveying line without providing a transporting unit for each analyzer.

Control Device 4 Configuration

As shown in FIG. 1, the control device 4 is configured by a personal computer (PC) 401 and the like, and includes a controller 4a, display unit 5c, and keyboard 4c. The controller 4a controls the operations of the measuring unit 2 and the transporting unit 3, and has the functions of analyzing the optical information of the sample obtained by the measuring unit 2. The controller 4a is configured by a CPU, ROM, RAM and the like. The display unit 4b is provided to display the analysis results obtained by the controller 4a, and to display the maintenance record and the like of the analyzer 1.

Figure 4:
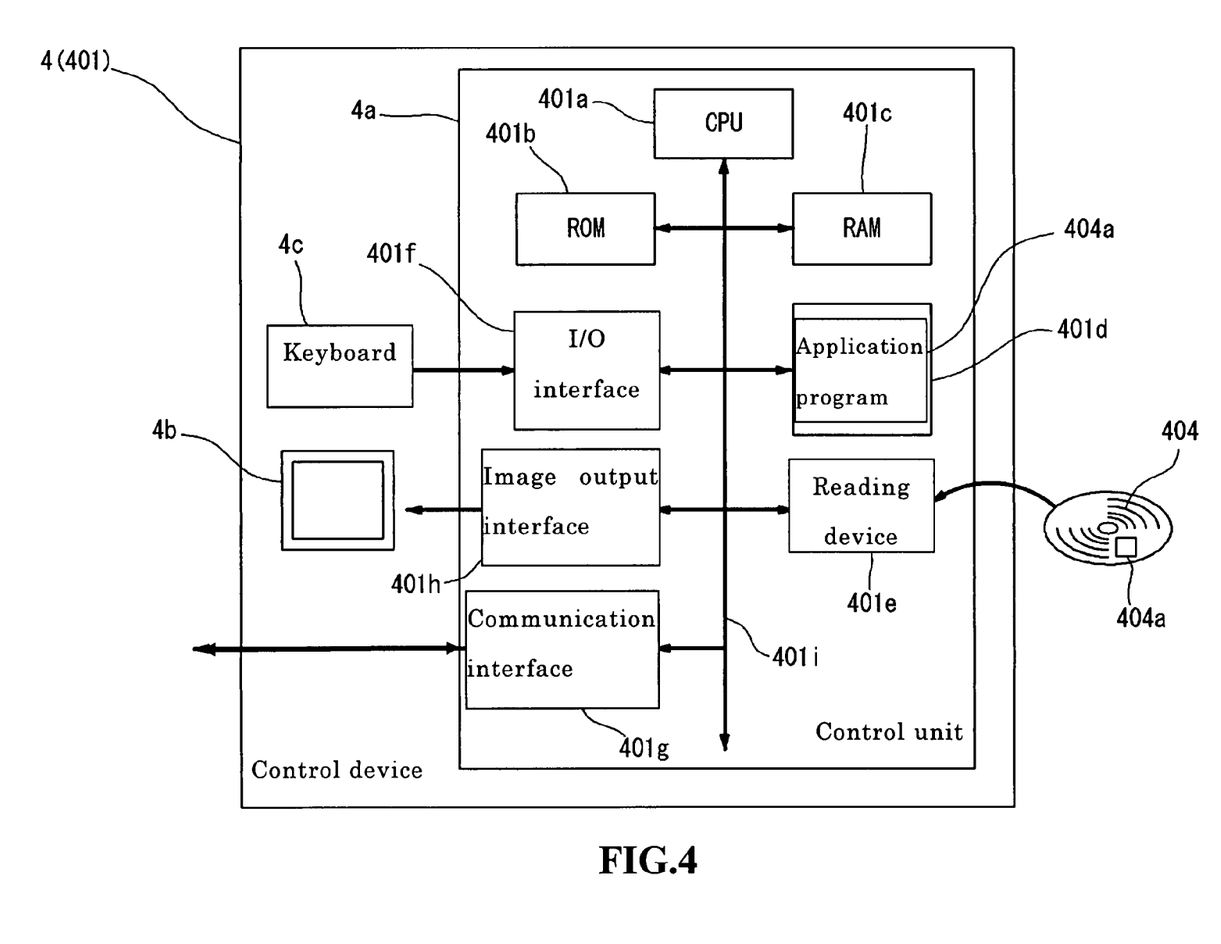
FIG. 4 is a block diagram of the control device in the sample measuring apparatus.

FIG. 4 is a block diagram of the control device 4 in the analyzer 1. The control unit 4a is mainly configured by a CPU 401a, ROM 401b, RAM 401c, hard disk 401d, reading device 401e, input/output (I/O) device 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401a when these computer programs are being executed.

The hard drive 401d contains various installed computer programs to be executed by the CPU 401a such as an operating system and application program 404a and the like, as well as data used in the execution of these computer programs.

The reading device 401e is configured by a floppy disk drive, CD-ROM drive, DVD-ROM drive or the like, and is capable of reading the computer programs and data stored on a portable recording medium 404.

The I/O interface 401f is configured, for example, by a serial interface such as a USB, IEEE1394, RS232C or the like, a parallel interface such as SCSI, IDE, IEEE1284 or the like, or an analog interface such as a D/A converter, A/D converter or the like. The keyboard 4c is connected to the I/O interface 401f, so that a user can input data in the computer 401 using the keyboard 4c.

The communication interface 401g is, for example, an Ethernet (registered trademark) interface. The computer 401 can send and receive data to and from the measuring device 2 via the communication interface 401g using a predetermined communication protocol.

The image output interface 401h is connected to the display unit 4b which is configured by an LCD, CRT or the like, so that image signals corresponding to the image data received from the CPU 401a can be output to the display unit 4b. The display unit 4b displays images (screens) in accordance with the input image signals.

Transporting Unit 3 Configuration

As shown in FIG. 1, the transporting unit 3 functions to transport a rack 151 that holds a plurality (ten in the present embodiment) of test tubes 150 which contain samples to an aspirating position 2a of the measuring unit 2 so as to supply sample to the measuring unit 2. Furthermore, the transporting unit 3 has a rack placement region 3a which accommodates the racks 151 that hold the test tubes 150 containing unprocessed specimens, and a rack receiving region 3b which accommodates the racks 151 that hold test tubes 150 containing processed specimens.

Measuring Unit 2 Configuration

The measuring unit 2 is capable of obtaining optical information related to a supplied sample by optically measuring the sample supplied from the transporting unit 3. In the present embodiment, a sample is dispensed from the test tube 150 disposed in the rack 151 of the transporting unit 3 into a cuvette 152 (refer to FIG. 2) of the measuring unit 2, and the dispensed sample is then optically measured. Furthermore, the measuring unit 2 is provided with a cuvette supplier 10, rotating unit 20, sample dispensing arm 30, HIL detecting unit 40, lamp unit 50, two reagent dispensing arms 60, cuvette transporter 70, detecting unit 80, rush sample acceptor 90, cuvette disposal unit 100, fluid provider 110, and a control unit 120 (FIG. 3), as shown in FIGS. 1 and 2.

The cuvette supplier 10 is configured to sequentially supply a plurality of cuvettes 152, which have been directly inserted by a user, to the rotating unit 20. As shown in FIG. 2, the cuvette supplier 10 includes a hopper 12 which is mounted on the device body via a bracket 11 (refer to FIG. 1), two induction plates 13 which are provided below the hopper 12, a support base 14 which is disposed at the bottom end of the two induction plates 13, and a catcher unit 15 which is provided at a predetermined distance from the support base 14. The two induction plates 13 are disposed so as to be mutually parallel with a space therebetween so the space is smaller than the diameter of the flange of the cuvette 152 and larger than the diameter of the barrel of the cuvette 152. The cuvettes 152 which have been supplied into the hopper 12 are configured so as to move smoothly while dropping toward the support base 14 with the flange engaged at the top surface of the two induction plates 13. Furthermore, the support base 14 functions to rotate the cuvette 152 that has dropped between the induction plates 13 to a position at which the cuvette 152 can be grabbed by the catcher unit 15. The catcher unit 15 is provided to supply the cuvette 152, which has been moved by the support base 14, to the rotating unit 20.

The rotating unit 20 is provided to transport, in a circular direction, those cuvettes 152 which have been received from the cuvette supplier 10, as well as reagent containers (not shown in the drawings) accommodating reagent to be added to the sample in the cuvette 152. As shown in FIG. 2, the rotating unit 20 is configured by a circular reagent table 21, an annular reagent table 22 which is disposed on the outer side of the circular reagent table 21, an annular secondary dispensing table 23 which is disposed on the outer side of the circular reagent table 22, and an annular primary dispensing table 24 disposed on the outer side of the circular secondary dispensing table 23. The primary dispensing table 24, secondary dispensing table 23, and reagent tables 21 and 22 are configured so as to be mutually and independently rotatable in both clockwise and counter clockwise directions.

Figure 2:
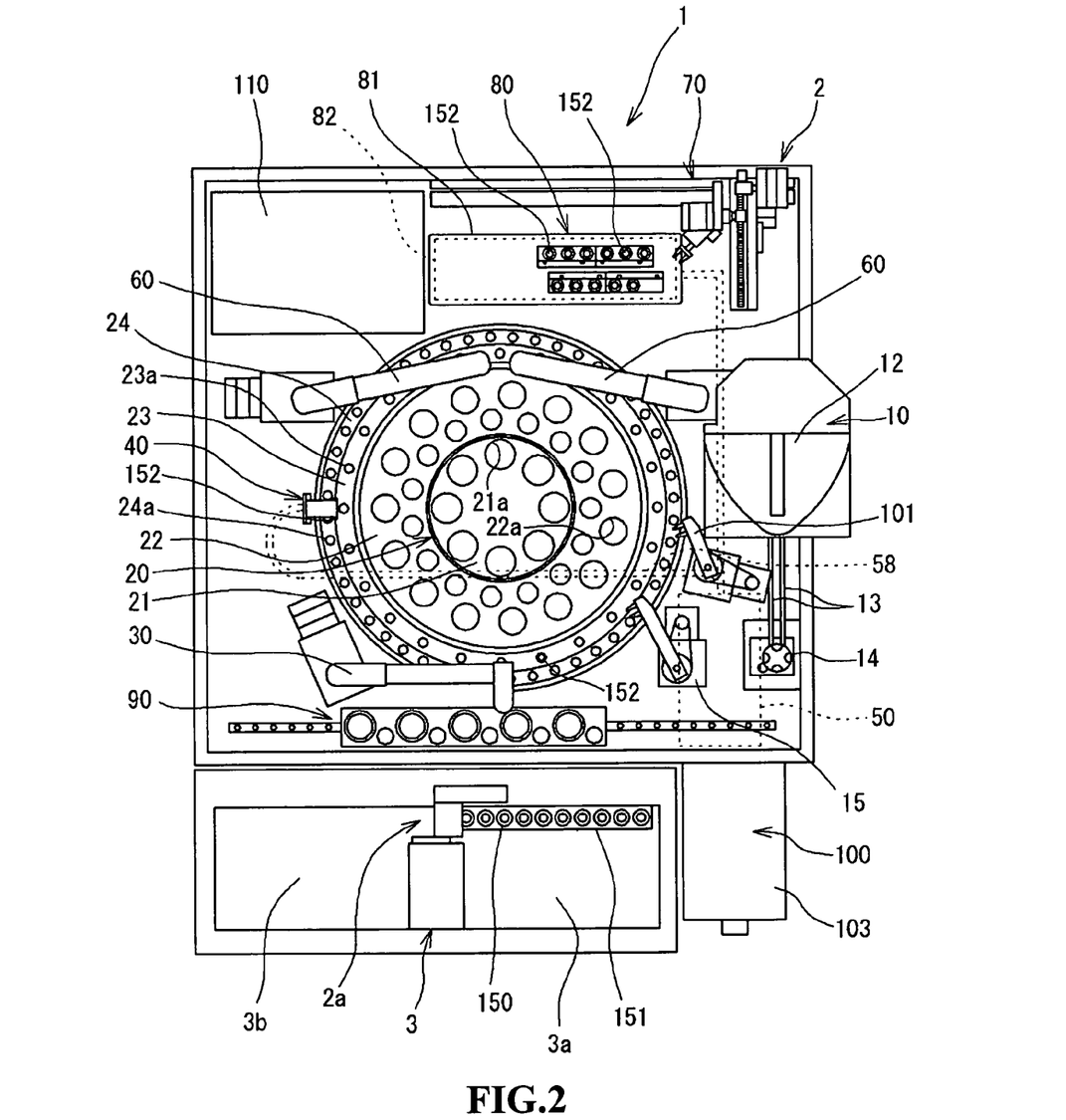
FIG. 2 is a top view of the measuring unit and transporting unit in the sample measuring apparatus.

As shown in FIG. 2, the reagent tables 21 and 22 respectively include a plurality of holes 21a and 22a provided at predetermined spacing in the circumferential direction. The holes 21a and 22a of the reagent tables 21 and 22 are provided to load a plurality of reagent containers (not shown in the drawings) that hold various reagents to be added when preparing measurement samples from specimens. Furthermore, the primary dispensing table 24 and secondary dispensing table 23 respectively include a plurality of cylindrical holders 24a and 23a which are provided at predetermined spacing in the circumferential direction. The holders 24a and 23a are provided to hold the cuvettes 152 received from the cuvette supplier 10. A sample contained in a test tube 150 of the transport unit 3 is dispensed to a cuvette 152 held by the holder 24a of the primary dispensing table 24 in a primary dispensing process. Furthermore, a sample contained in the cuvette 152 loaded in the primary dispensing table 24 is dispensed to a cuvette 152 loaded in the holder 23a of the secondary dispensing table 23 in a secondary dispensing process. A pair of holes are formed in the holder 24a at mutually facing positions on the sides of the holder 24a. The pair of holes are provided for the passage of light emitted from a beam splitter optical fiber 58 of the lamp unit 50, which is described later.

The sample dispensing arm 30 functions to both aspirate a sample contained in a test tube 150 which has been transported to the aspiration position 2a via the transport device 3, and to dispense the aspirated sample into a cuvette 152 which has been transported to the rotating unit 20.

The HIL detecting unit 40 is configured so as to acquire optical information from a sample in order to measure the presence and concentration of interference substances (chyle, hemoglobin, bilirubin) in the sample before adding reagent. Specifically, the presence and concentrations of interference substances are measured using four types of light (405 nm, 575 nm, 660 nm, 800 nm) among five types of light (340 nm, 405 nm, 575 nm, 660 nm, 800 nm) emitted from the lamp unit 50, which is described later. The 405 nm wavelength light is absorbed by chyle, hemoglobin, and bilirubin. That is, chyle, hemoglobin, and bilirubin influence the optical information measured using light at a wavelength of 405 nm. Furthermore, light at a wavelength of 575 nm is absorbed by chyle and hemoglobin, although this light is essentially not absorbed by bilirubin. That is, chyle and hemoglobin influence the optical information measured using light at a wavelength of 575 nm. Light at wavelengths of 660 nm and 800 nm are absorbed by chyle, although these wavelengths essentially are not absorbed by bilirubin and hemoglobin. That is, chyle influences the optical information measured using light at wavelengths of 660 nm and 800 nm. Chyle absorbs light from the low wavelength region of 405 nm to the high wavelength region of 800 nm, with chyle absorbing more light at the 660 nm wavelength than at the 800 nm wavelength. That is, the optical information measured using light at the 800 nm wavelength is less influenced by chyle than optical information at the 660 nm wavelength.

The acquisition of sample optical information by the HIL detecting unit 40 occurs before optically measuring (main measurement) the sample by the detecting unit 80. As shown in FIG. 2, the HIL detecting unit 40 obtains optical information from the sample within the cuvette 152 which is held by the holder 24a of the primary dispensing table 24.

In the present embodiment, the lamp unit 50 is provided to supply the light to be used in the optical measurements performed by the HIL detecting unit 40 and the detecting unit 80, as shown in FIG. 2. That is, a single lamp unit 50 is configured so as to be used jointly by the HIL detecting unit 40 and the detecting unit 80.

As shown in FIGS. 1 and 2, the reagent dispensing arm 60 is provided to dispense the reagent within a reagent container (not shown in the drawings), which has been loaded on the rotating unit 20, into a cuvette 152 held in the rotating unit 20. In this way a measurement sample is prepared by adding reagent to a sample after the sample has been optically measured by the HIL detecting unit 40. The cuvette transporter 70 is provided to move the cuvette 152 between the rotating unit 20 and the detecting unit 80. A heating pipette, which configures a heating device provided with a reagent heating function, is mounted on the tip of the reagent dispensing arm 60.

The detecting unit 80 functions to heat the measurement sample which has been prepared by adding reagent to a sample, and to measure optical information from the measurement sample. As shown in FIG. 2, the detecting unit 80 is configured by a cuvette loader 81, and a detection unit 82 disposed below the cuvette loader 81.

Figure 5:
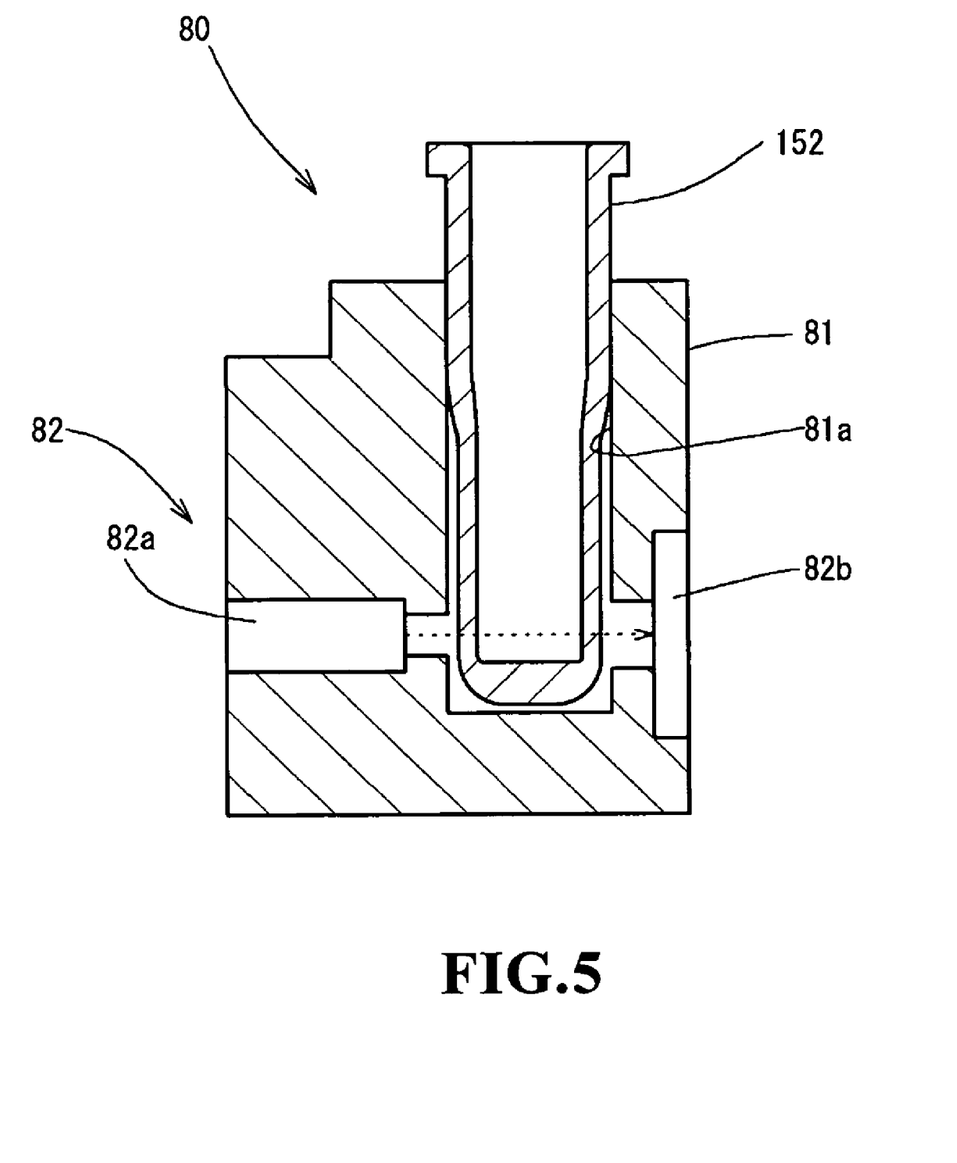
FIG. 5 is a cross section view of the detection unit in the sample measuring apparatus.

FIG. 5 is a cross section view of the detecting unit 80. A plurality of insertion orifices 81a are formed in the cuvette loader 81 so that cuvettes 152 can be loaded into the insertion orifices 81a. The detecting unit 82 has a light source 82a and a photoelectric conversion element 82b, so that light emitted from the light source 82a is transmitted through the cuvette 152 and is received by the photoelectric conversion element 82b. An LED may be used as the light source 82a, and a photodiode may be used as the photoelectric conversion element 82b. The cuvette loader 81 may also be provided with insertion orifices which are provided with a heating function (not shown in the drawing).

As shown in FIGS. 1 and 2, the rush sample acceptor 90 is provided to perform a sample analysis process on a sample which requires immediate processing. The rush sample acceptor 90 is capable of performing an interrupt on behalf of a rush sample when there is an on-going sample analysis process being performed on a sample supplied from the transport unit 3. The cuvette disposal unit 100 is provided to dispose of cuvettes 152 from the rotating unit 20. As shown in FIG. 2, the cuvette disposal unit 100 is configured by a waste unit 101, a disposal orifice 102 which is provided at predetermined spacing from the waste unit 101 (refer to FIG. 1), and a waste box 103 which is provided below the disposal hole 102. The waste unit 101 is provided to move a cuvette 152 from the rotating unit 20 to the waste box 103 via the disposal orifice 102 (refer to FIG. 1). A fluid provider 110 is provided to supply a liquid, such as cleaning liquid or the like, to a nozzle provided on each dispensing arm during the shutdown process of the sample analyzer 1.

Figure 3:
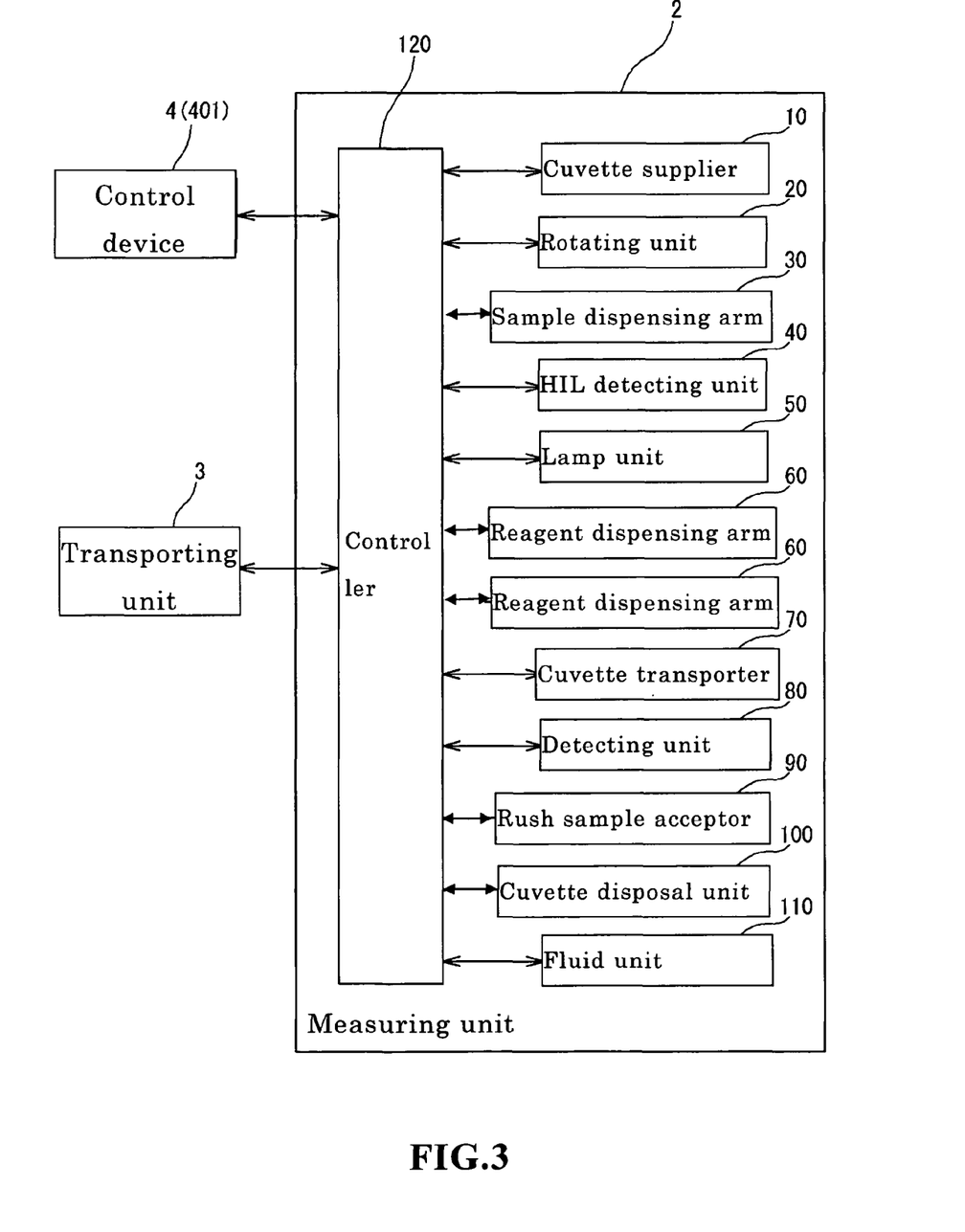
FIG. 3 is a block diagram showing the configuration of the measuring unit in the sample measuring apparatus.

FIG. 3 is a block diagram showing the configuration of the measuring unit 2. The cuvette supplier 10, rotating unit 20, sample dispensing arm 30, HIL detecting unit 40, lamp unit 50, two reagent dispensing arms 60, cuvette transporter 70, detecting unit 80, rush sample acceptor 90, cuvette disposal unit 100, and fluid provider 110 are connected to the control unit 120 so as to be capable of communicating electrical signals. The control unit 120 is configured by a CPU, ROM, RAM and the like, and controls the operations of each mechanism by the CPU executing a control program previously stored in the ROM.

Sequence of the Sample Analysis Operation

The sample analysis operation performed by the sample analyzer 1 is described below. The measurement item is the plasma thrombin time (TT). This item measures the time from the addition of thrombin reagent to the plasma until the coagulation occurs by monitoring the process during which the fibrinogen is converted to fibrin.

Figure 6:
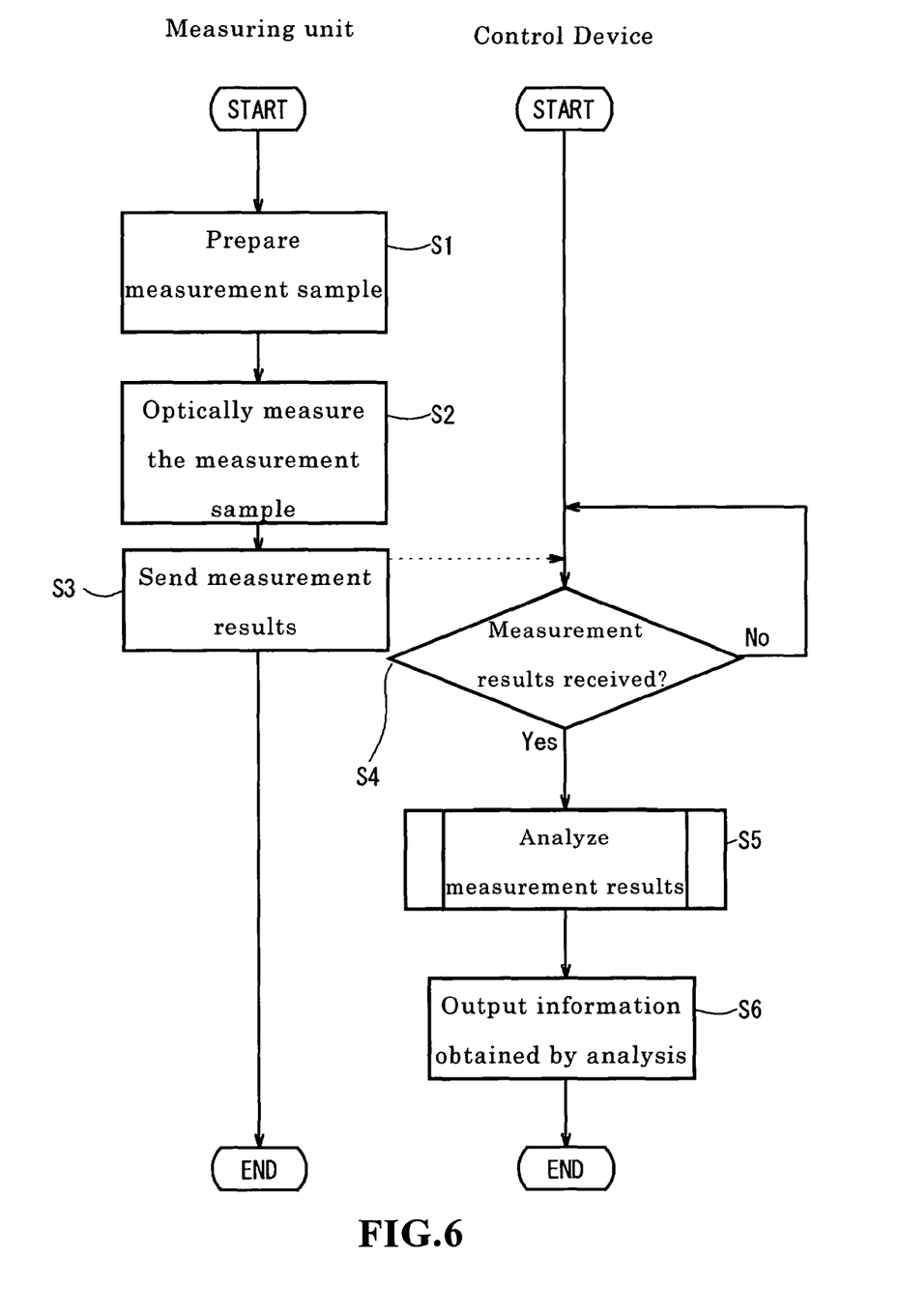
FIG. 6 is a flow chart showing the sequence of the sample measuring operation of the sample measuring apparatus.

FIG. 6 is a flow chart showing the sequence of the sample analysis operation performed by the sample analyzer 1. A measurement sample is first prepared in step S1. As shown in FIG. 2, the sample dispensing arm 30 aspirates a predetermined amount of the sample, which is within a test tube 150 that has been transported to the aspirating position 2a of the measuring unit 2 by the transporting unit 3, and dispenses the aspirated sample into a cuvette 152 which has been loaded in the rotating unit 20. The rotating unit 20 moves the cuvette 152, which contains the predetermined amount of sample that was dispensed by the sample dispensing arm 30, to a predetermined position. The cuvette 152, which has been moved to the predetermined position by the rotating unit 20, is then carried to the detecting unit 80 by the cuvette transporter 70, where the cuvette 152 is loaded into an insertion orifice which has a heating function to be heated for a set time. Thereafter, the cuvette 152 is removed from the insertion orifice by the cuvette transporter 70, and reagent is added to the sample within the cuvette 152 by the reagent dispensing arm 60 to prepare a measurement sample.

In step S2 of FIG. 6, the measurement sample within the cuvette 152 is optically measured. The cuvette 152 containing the measurement sample is then moved again to the detecting unit 80 by the cuvette transporter 70, and loaded in the insertion orifice 81a shown in FIG. 5. The cuvette 152, which has been loaded into the insertion orifice 81a, is irradiated by light emitted from the light source 82a, and the light which is transmitted through the measurement sample within the cuvette 152 is received by the photoelectric conversion element 82b, which converts this light to electrical signals that correspond to the intensity of the light. The electrical signal are then converted to digital signals by an A/D conversion unit (not shown in the drawing). Thus, the measurement sample is optically measured and the data associated with the amount of transmission light for a predetermined time and the data associated with the time during which the transmission light was measured are obtained as measurement results.

In step S3 of FIG. 6, the controller 120 of the measuring unit 2 (refer to FIG. 3) sends the measurement results obtained in step S2 through a communication interface, which is not shown in the drawing, to the controller 4a of the control device 4 (FIG. 4).

In step S4 of FIG. 6, the measurement results which were transmitted in step S3 are received by the controller 4a of the control device 4 through the communication interface 401g (FIG. 4), and the CPU 401a confirms whether or not the measurement results have been stored a memory unit such as the RAM 401c or the like. When reception of the measurement results has been confirmed, the routine advances to step S5.

The measurement results obtained in step S2 are analyzed in step S5. Details of the analysis are described below. The information obtained via the analysis performed in step S5 is output in step S6. Steps S5 and S6 are both performed by the control device 4.

Detailed Sequence of the Analysis Step

Figure 7:
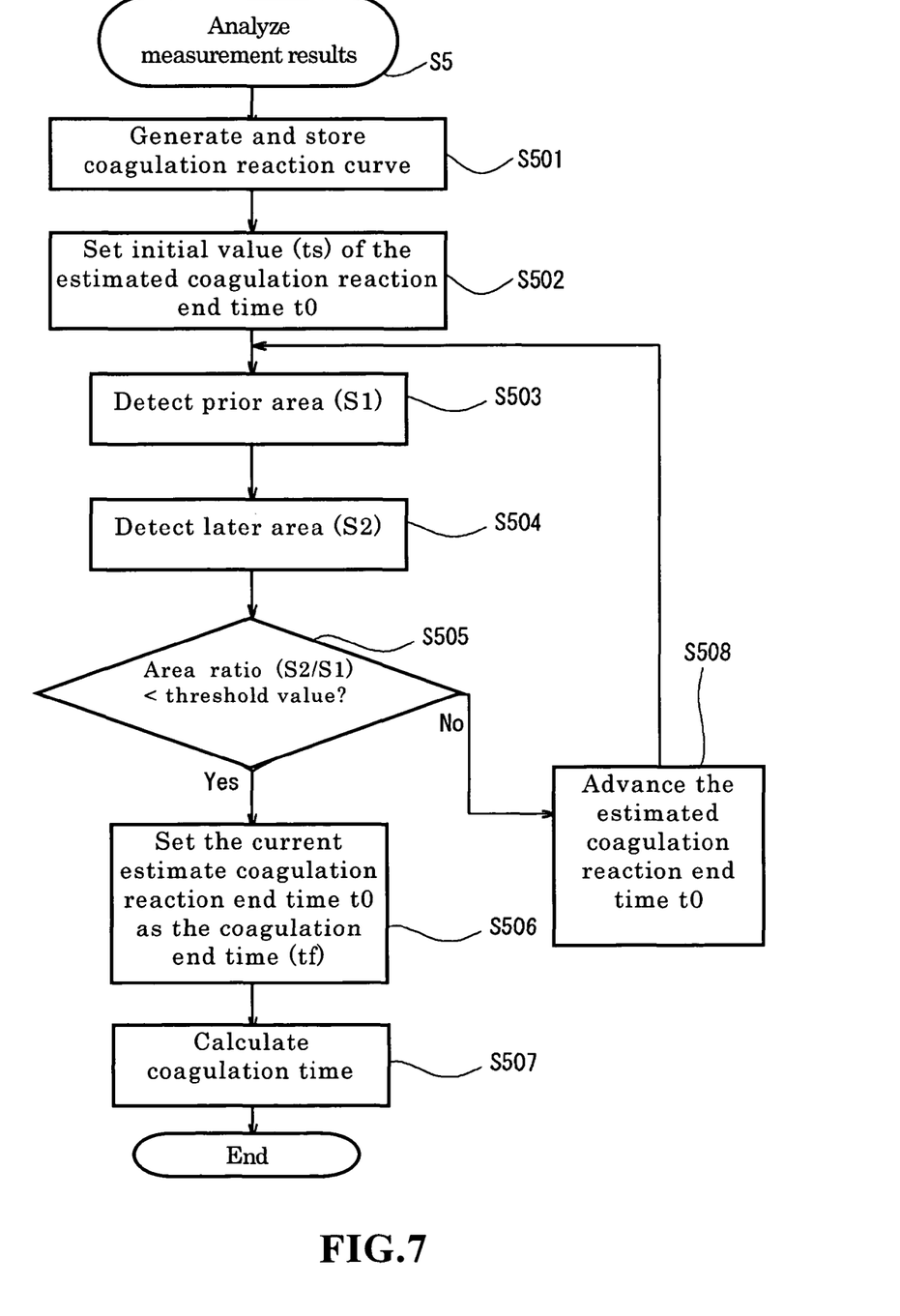
FIG. 7 is a flow chart showing the sequence of the sample measuring operation of the sample measuring apparatus.

FIG. 7 is a flow chart which shows details of the analysis sequence performed in step S5 of FIG. 6.

Figure 8:
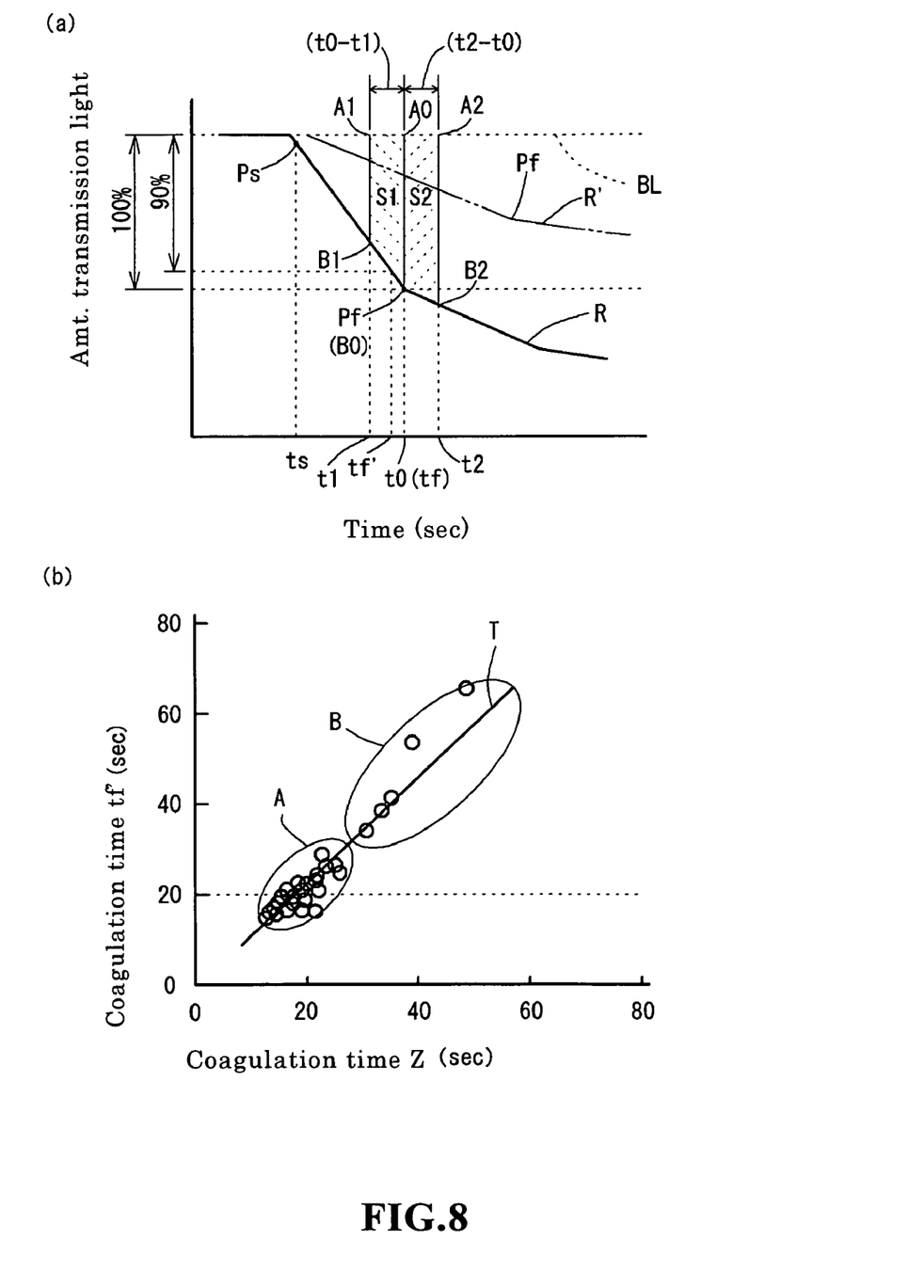
FIG. 8(a) is a graph showing a coagulation reaction curve.
FIG. 8(b) is a graph showing the relationship between the coagulation reaction curve and the coagulation time measured by another measuring apparatus.

Step S501 generates a coagulation reaction curve which represents the change in the amount of transmission light over time based on the measurement results obtained in step S2, and stores the curve in a memory unit such as the RAM 401c of the controller 4a (FIG. 4). FIG. 8(a) shows an example of a coagulation reaction curve R plotted on two dimensional coordinates in which the horizontal axis is the time axis and the vertical axis is the transmission light.

In the case of the example coagulation reaction curve R, a large amount of light is transmitted immediately after the reagent was added and there is scant change observed soon thereafter. As the reaction progresses, however, fibrin mass begins to form and the measurement sample becomes turbid with the amount of transmission light rapidly decreasing in conjunction with the formation of fibrin. When the coagulation reaction is nearly completed, the change in transmission light intensity becomes quite small and remains nearly constant thereafter.

Changes in the coagulation reaction curve R are evident in the steep slope in the range from the origin point Ps to point Pf, then a more moderate slope in the range after point Pf. That is, the point Pf is an inflection point of the coagulation reaction curve R.

The plasma coagulation reaction can be considered to end at the inflection point Pf by investigations using other coagulation measurement methods (for example, a visco-elasticity measurement method). That is, dense fibrin masses are formed by the actual coagulation reaction prior to the inflection point Pf, which causes a precipitous drop in the amount of transmitted light. After the inflection point Pf, however, micro fibrin masses are formed by the remaining fibrinogen so that more moderate decrease in the amount of transmitted light occurs. Coagulation is, of course, not affected much by the continuing increase of the micro fibrin masses.

In the present embodiment, the time tf at which the inflection point Pf occurs, that is the end point of the actual coagulation reaction, is directly identified, and the an accurate coagulation time can be determined using the time tf. The coagulation time is determined by performing the following sequence.

An initial value (ts) of the estimated coagulation reaction end time t0 is first set in step S502.

Then, the area (first area) represented by S1 in FIG. 8(a) is determined at the initial value (ts) of the estimated coagulation reaction end time t0 in step S503 of FIG. 7, and the area (second area) represented by S2 is determined in step S504.

Specifically, the difference between the measurement value of the transmission light is first calculated at a predetermined time from the start of measurement, and a change in the measurement value is indicated when this difference is greater than a predetermined value; that is, the coagulation reaction is determined to have started by this difference, and the time is set as the coagulation reaction starting time ts. The measurement value of the highest amount of transmission light during several seconds after measurement starts is set as a standard value and, at the standard value, a fixed line extending along the horizontal axis is set as a baseline BL.

An optional time after the coagulation starting time ts is set as the "estimated" coagulation reaction end time (evaluation target time) t0, which is used to evaluate whether or not the coagulation reaction end time has been reached. The area S1 is set as the area circumscribing the coagulation reaction curve R and the baseline BL in the region from the coagulation reaction starting time t0 to an earlier time (first time t1) (step S503). Then, the area S2 is set as the area circumscribing the coagulation reaction curve R and the baseline BL in a region from the coagulation reaction starting time ts to a later time (second time t2) (step S504).

That is, the area S1 is the area stipulated by four points including a point A0 on the baseline BL and point B0 on the coagulation reaction curve R at the estimated coagulation reaction end time t0, and point A1 on the baseline BL at the first time t1 and point B1 on the coagulation reaction curve R. A straight line from point B0 to point B1 approaches a straight line from point B0 to point B1 of the coagulation reaction curve R.

Similarly, the area S2 is the area stipulated by four points including a point A0 and point B0, and point A2 on the baseline BL and point B2 on the coagulation reaction curve R at the first time t2. A straight line from point B0 to point B2 approaches a straight line from point B0 to point B2 of the coagulation reaction curve R.

The coagulation curve R is not a smooth curve since the amount of transmitted light fluctuates up and down at short intervals. Therefore, when the coagulation reaction curve approaches a straight line at short intervals and the areas S1 and S2 are determined, there will be times when the volume ratio (S2/S1), which is described later, is unstable due to the influence of the fluctuations of the transmission light. The interval (t0-t1) and the interval (t2-t0) must therefore be set so as to ensure an adequate time to absorb the fluctuations in the transmission light at short intervals on the coagulation reaction curve R.

Moreover, with the baseline BL set as standard, each area S1 and S2 represent the amount of thrombin generated in the interval (t0-t1) and the interval (t2-t0), respectively.

In step S505 of FIG. 7, a determination is made as to whether or not the area ratio (S2/S1) is less than a predetermined threshold value. When the area ratio (S2/S1) is less than the predetermined threshold value, the routine continues to step S506 and the estimated coagulation reaction end time t0 is set as the coagulation reaction end time tf.

When the coagulation reaction end time tf has been determined, the coagulation time tf' is determined based on the coagulation starting time ts and the coagulation reaction end time tf in step S507.

Specifically, when the amount of change between the highest transmission light on the coagulation reaction curve R (baseline position) and the transmission light at the coagulation reaction end time tf is set at 100%, the time tf' at which the amount of change is 90% is set as the coagulation time.

The estimated coagulation reaction end time t0 is sequentially reset at predetermined time intervals using the coagulation starting time ts as the starting point until the coagulation reaction end time tf has been determined. That is, the estimated coagulation reaction end time t0 is not determined to be the coagulation reaction end time tf when the area ratio (S2/S1) is greater than the predetermined threshold value in step S505 of FIG. 7, and the estimated coagulation reaction end time t0 is reset to a new estimated coagulation reaction end time t0 at predetermined time intervals in step S508. Then, the processes of steps S503 through S505 are repeated using the new estimated coagulation reaction time end time t0.

During the above processes in the resent embodiment, the control device 4 performs a generation process to generate a coagulation reaction curve which represents the change in the amount of transmitted light over time, a determination process to determine the first and second areas S1 and S2 formed between the baseline BL and the coagulation reaction curve R which are regions of time from the estimated coagulation reaction end time t0 (evaluation target time), which is a standard, and a previous time t1 and a later region of time to t2 to determine the coagulation reaction end time tf based on the first and second areas S1 and S2, and an acquisition process to obtain the coagulation end time tf' which is characteristics of the sample based on the determined coagulation reaction end time tf. That is, the control device 4 can be said to be a generating means, determining means, and acquiring means which respectively perform the generation process, determination process, and acquisition process.

Threshold Values

In FIG. 8(a), when the estimated coagulation reaction end time t0 is set in the range from point Ps to point Pf and the areas S1 and S2 are determined, there is an increase in the ratio of areas S1 and S2 due to the steep slope of the coagulation reaction curve R. However, when the time of the inflection point Pf is set as the estimated coagulation reaction end time t0, the ratio of the areas S1 and S2 becomes acutely smaller than the area ratio determined in the region prior to the inflection point Pf. Therefore, the area ratio (S2/S1) prior to the inflection point Pf and the area ratio (S2/S1) after the inflection pint Pf can be clearly distinguished. The threshold value is suitably set as a value which can identify this change.

In view of the above, the threshold value is set based on results of numerous measurements of samples for each item and control substances (experimental values). For example, the threshold value may be set as a numeric value of approximately 1.2 to 1.8. Furthermore, the threshold value changes depending on the type of reagent and the item to be measured.

Interval (t0-t1) and Interval (t2-t0)

The interval (t0-t1) and the interval (t2-t0), which are set by determining the areas S1 and S2, are variable so as to change according to the measurement item.

Figure 10:
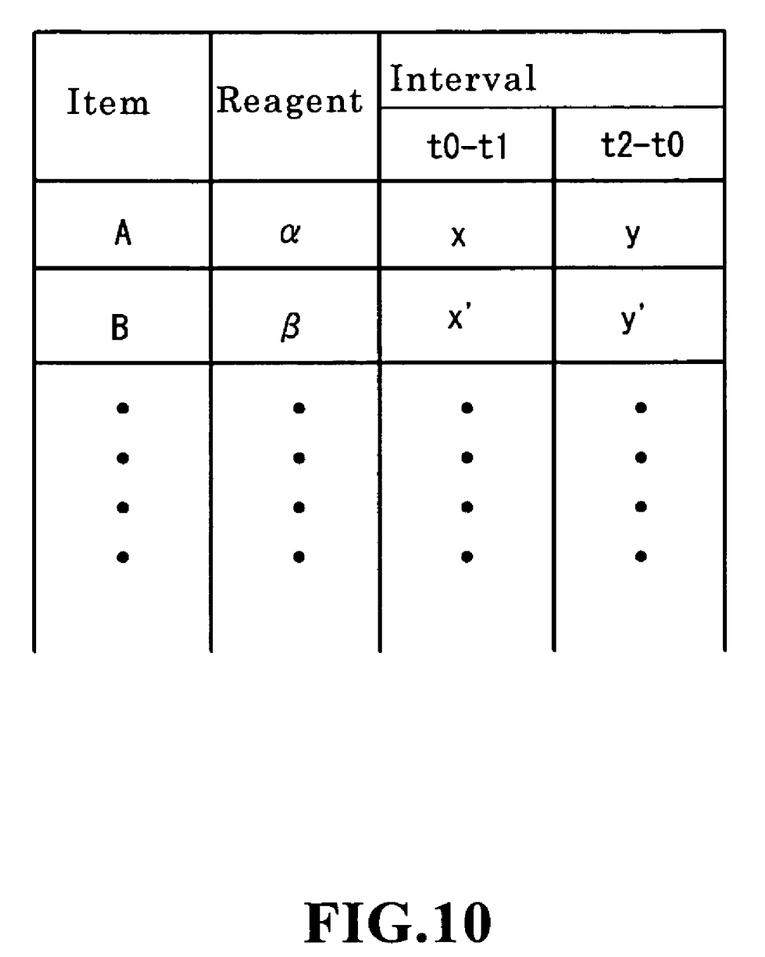
FIG. 10 is a table used to determine time intervals (t0-t1) and (t2-t0).

FIG. 10 is a table for setting the interval (t0-t1) and the interval (t2-t0); this table is stored beforehand in the memory unit of the control device 4. When measurement is started by the analyzer 1 and a measurement item is input from the keyboard 4c (FIG. 1) of the control device 4, the control device 4 refers to the table and selects reagents corresponding to the input measurement item, and sets the interval (t0-t1) and the interval (t2-t0). Reagent a and intervals x and y are set when item A is selected in the example shown in FIG. 10, whereas reagent β and intervals x' and y' are set when item B is selected. Furthermore, the threshold value is similarly set according to the measurement item.

Effects of the Present Embodiment

As described above, not only is the change in the coagulation reaction curve R (inflection point Pf) determined based on the change in the transmission light over a predetermined time (that is, based on the slope of the coagulation reaction curve R) in the present embodiment, noise affecting the areas S1 and S2 is reduced to more accurately determine the inflection point Pf regardless of the fluctuations in the transmission light measurement values due to such noise because the change in the coagulation reaction curve R is measured based on the change in the change in the areas S1 and S2 using a specific time t0 as a basis.

Although a coagulation reaction curve R' is generated which has a more moderately extended slope than the coagulation reaction curve R shown in FIG. 8(a) occurs for samples which have an abnormally low fibrinogen value, the actual coagulation reaction end time (inflection point Pf) can also be determined using the coagulation reaction curve R' to obtain the coagulation time.

There are some samples (for, example, samples with high concentration of fibrinogen and heparin samples) in which optical changes can be observed to continue regardless of the end of the actual coagulation reaction, however, the inflection point Pf can be accurately determined at the intermediate stages of the optical changes.

In FIG. 8(a), the coagulation time is not the time tf at the inflection point Pf, but rather is the prior time tf' (at which point the change in the transmission light is 90%). This allows using, as a basis, a time at which the obtained measurement value is more stable than the inflection point Pf at which there is a large change in the coagulation reaction curve R. Setting the time tf' prior to the inflection point Pf rather than after the inflection point Pf suppresses errors diverging from the standard coagulation time because less change occurs during the time prior to the inflection point Pf than during the time after the inflection point Pf.

In the present invention, any time between the coagulation starting time ts and the inflection point Pf may be set as the coagulation time tf'.

Evidence Supporting the Effects of the Present Embodiment

FIG. 8(b) plots on a single graph the coagulation times tf' and Z obtained by the sample analyzer 1 of the present embodiment and another analyzer (for example, an analyzer which measures visco-elasticity) using identical samples. Using the coagulation time Z obtained by the other analyzer as a reference, the coagulation time tf' of the present embodiment can be evaluated as accurate if the coagulation time tf' matches the coagulation time Z.

Figure 9:
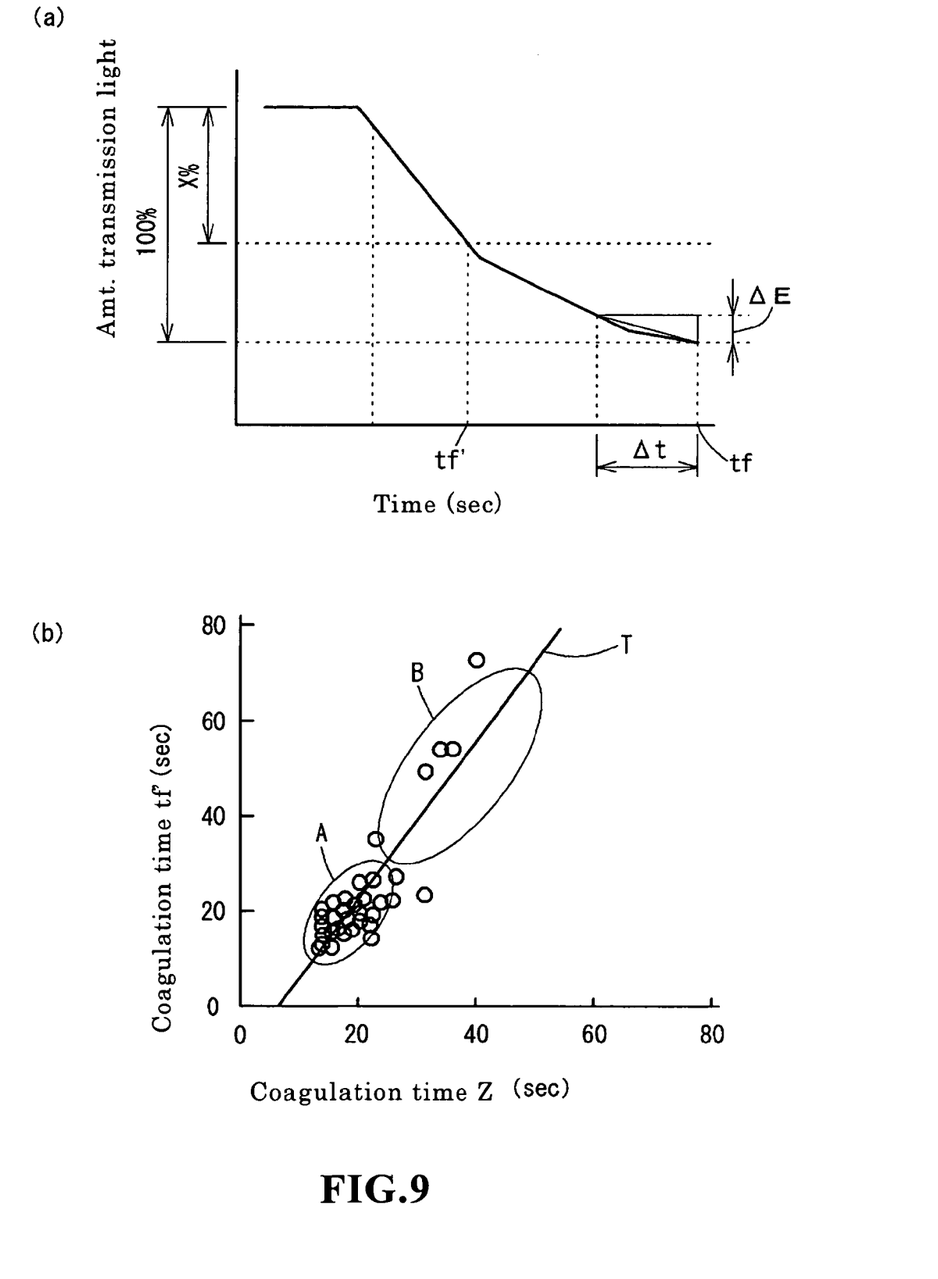
FIG. 9(a) is a graph showing a coagulation reaction curve of a comparative example (conventional art)
FIG. 9(b) is a graph showing the relationship between the coagulation reaction curve and the coagulation time measured by another measuring apparatus.

As a comparative example, FIG. 9(b) shows the coagulation time tf' measured using a conventional method and a coagulation time Z used as a reference plotted on a single graph. As shown in FIG. 9(a), the conventional method sets a time in which the change is x % (for example, x=50) as the coagulation time tf' when the change ΔE in the transmission light per predetermined time Δt is determined, the time during which this change (ΔE/Δt) is less than a predetermined threshold value is set as the coagulation reaction end time tf, and the change in transmission light from the coagulation reaction starting time to the coagulation reaction end time tf is set as 100%.

The straight line T in FIGS. 8(b) and 9(b) closely matches the coagulation time Z and coagulation time tf'.

There is a divergence from the coagulation times Z and tf' in FIG. 9(b) which widens vertically from line T, particularly near region A, compared to FIG. 8(b). When, for example, a line at 20 seconds is set as a threshold and placement below the line is judged a normal sample and placement above the line is judged an abnormal sample, a sample may be deemed normal if the coagulation time Z is used as a basis, but the same sample may be deemed abnormal using the coagulation time tf' as a basis, and the converse may also often be true. An index capable of determining that a normal sample is a normal sample will have excellent specificity, and the specificity is approximately 76% in the case of the comparative example shown in FIG. 9(b).

Conversely, the present embodiment can be understood to determine a more accurate coagulation time tf' since there is scant divergence of the coagulation times Z and tf' at line T as shown in FIG. 8(b). The specificity is approximately 93% in the present embodiment, which is a very high value in comparison to that of the comparative example.

The present invention is not limited to the embodiment described above, and may be suitably modified in design. For example, the present invention is not limited to the measurement of thrombin time of blood plasma inasmuch as other items (PT, PATT, LA, Fbg and the like) may be measured. Furthermore, the present invention may also be used to measure items other than the blood coagulation time, for example, the measurement of platelet aggregation time.

The baseline BL may be optionally set as a fixed line which is parallel to the time axis. When thrombin time is measured, however, it is desirable that the baseline is set so that the area between the baseline BL and the coagulation reaction curve R represents the amount of thrombin generated (the baseline which has been clearly described in the above embodiment).

The interval (t0-t1) and the interval (t2-t0) may be identical values or different values.

Although the area ratio of the first and second areas S1 and S2 is compared to a predetermined threshold value in the above embodiment, the coagulation reaction end time may also be determined by comparing the area differential of the first and second areas S1 and S2 to a predetermined threshold value.

The present invention is not limited to blood samples, and may also be used as a measuring device for other samples.

Although the area S1 is stipulated by four points including point A0, point B0, point A1, and point B1, and a coagulation reaction curve R which approaches a straight line between point B0 and point B1 is used in the above embodiment, a coagulation reaction curve R which approximates a line between point B0 and point B1 (for example and approximation curve) may also be used.

Similarly, although the area S2 is stipulated by four points including point A0, point B0, point A2, and point B2, and a coagulation reaction curve R which approaches a straight line between point B0 and point B2 is used in the above embodiment, a coagulation reaction curve R which approximates a line between point B0 and point B2 (for example and approximation curve) may also be used.

Although the areas between the baseline BL and the coagulation reaction curve R are set as S1 and S2 in the above embodiment, the baseline BL may be set on the time axis, and the areas between the time axis and the coagulation reaction curve R may be set as S1 and S2.

Although the coagulation reaction curve R is approximated in the above embodiment, approximation is unnecessary if the intervals (t0-t1) and (T2-t0) are set greater than a predetermined value.

What is claimed is:

1. A sample analyzer comprising:
   a measuring means for optically measuring reaction of a sample mixed with reagent, and obtaining optical information therefrom;
   a generating means for generating a reaction curve representing change in the optical information over time;
   a determining means for determining a first area prior to an evaluation target time (t0) and a second area after the evaluation target time (t0) wherein the first and second areas are formed between a baseline which is parallel to the time axis and a reaction curve from a first time (t1) prior to the optional evaluation target time (t0) to a second time (t2) after the evaluation target time, and determining the reaction end point based on the first and second areas; and
   an acquiring means for obtaining a characteristic of a sample based on the determined reaction end point.

2. The sample analyzer of claim 1, wherein
   the determining means determines the first and second areas as the evaluation target time (t0) sequentially changes, and determines a point on the reaction curve at the evaluation target time (t0) as the reaction end point when the first and second areas satisfy a predetermined condition.

3. The sample analyzer of claim 2, wherein
   the predetermined condition determines a relationship between the area ratio of the first and second areas and a predetermined threshold value.

4. The sample analyzer of claim 1, wherein
   the first area is stipulated by the points A0, B0, B1, A1, and the second area is stipulated by the points A0, B0, B2, A2 when a point on the baseline at the evaluation target time (t0) is designated A0, a point on the reaction curve at the evaluation target time (t0) is designated B0, a point on the baseline prior to a first time (t1) is designated A1, a point on the reaction curve prior to a first time (t1) is designated B1, a point on the baseline at a second time (t2) is designated A2, and a point on the reaction curve at a second time (t2) is designated B2.

5. The sample analyzer of claim 1, wherein
   an interval (t0-t1) from the first time (t1) to the evaluation target time (t0) and an interval (t2-t0) from the evaluation target time (t0) to the second time (t2) are variable, and a setting means is provided to set the intervals (t0-t1) and (t2-t0).

6. The sample analyzer of claim 5, wherein
   the setting means sets the intervals (t0-t1) and (t2-t0) in accordance with the sample measurement items.

7. The sample analyzer of claim 1, wherein
   an interval (t0-t1) from the first time (t1) to the evaluation target time (t0) and an interval (t2-t0) from the evaluation target time (t0) to the second time (t2) are identical.

8. The sample analyzer of claim 1, wherein
   the sample is a blood sample.

9. The sample analyzer of claim 1, wherein
   the optical information is the amount of light transmitted through the sample.

10. The sample analyzer of claim 1, wherein
    the reaction curve is a coagulation reaction curve.

11. The sample analyzer of claim 1, wherein
    the characteristic of the sample is the coagulation time.

12. A sample analyzing method comprising:
    a measuring step for optically measuring reaction of a sample mixed with reagent, and obtaining optical information therefrom;
    a generating step for generating, using a computer processor, a reaction curve which represents change in the optical information over time;
    a determining step for determining, using the computer processor, a first area prior to an evaluation target time t0 and a second area after the evaluation target time (t0) wherein the first and second areas are formed between a baseline which is parallel to the time axis and a reaction curve from a first time (t1) prior to the optional evaluation target time (t0) to a second time (t2) after the evaluation target time, and determining the reaction end point based on the first and second areas; and
    an acquiring step for obtaining, using the computer processor, a characteristic of a sample based on the determined reaction end point.

13. The sample measuring method of claim 12, wherein
    the determining step determines, using the computer processor, the first and second areas as the evaluation target time (t0) sequentially changes, and determines a point on the reaction curve at the evaluation target time (t0) as the reaction end point when the first and second areas satisfy a predetermined condition.

14. The sample analyzing method of claim 13, wherein
    the predetermined conditions determine a relationship between the area ratio of the first and second areas and a predetermined threshold value.

15. The sample analyzing method of claim 12, wherein
    the first area is stipulated by the points A0, B0, B1, A1, and the second area is stipulated by the points A0, B0, B2, A2 when a point on the baseline at the evaluation target time (t0) is designated A0, a point on the reaction curve at the evaluation target time (t0) is designated B0, a point on the baseline prior to a first time (t1) is designated A1, a point on the reaction curve prior to a first time (t1) is designated B1, a point on the baseline at a second time (t2) is designated A2, and a point on the reaction curve at a second time (t2) is designated B2.

16. A sample analyzer comprising:
    a means for optically measuring reaction of a sample mixed with reagent, and obtaining optical information therefrom;

a generating means for generating a reaction curve representing change in the optical information over time;

a determining means for determining a reaction end point based on a first value which represents an amount of a predetermined component generated by a reaction in the sample during a predetermined time period prior to an evaluation target time (t0), and a second value representing an amount of the predetermined component generated by a reaction in the sample during a predetermined time period after the evaluation target time (t0); and an acquiring means for obtaining a characteristic of a sample based on the determined reaction end point.

17. The sample analyzer of claim 16, wherein
the determining means determines the first and second values as the evaluation target time (t0) sequentially changes, and determines a point on the reaction curve at the evaluation target time (t0) as the reaction end point when the first and second values satisfy a predetermined condition.

18. The sample analyzer of claim 17, wherein
the predetermined conditions determine a relationship between the ratio of the first and second values and a predetermined threshold value.

19. The sample analyzer of claim 16, wherein
the first value is the area of a predetermined region prior to an evaluation target time (t0), and the second value is the area of a predetermined region after the evaluation target time (t0).

20. The sample analyzer of claim 16, wherein
the predetermined component is thrombin.

* * * * *